United States Patent [19]

Serrano Gonzalez

[11] Patent Number: 5,334,156
[45] Date of Patent: Aug. 2, 1994

[54] THROW-AWAY SYRINGE

[75] Inventor: Antonio Serrano Gonzalez, El Vedat de Torrent, Spain

[73] Assignee: Sanitor S.L., Madrid, Spain

[21] Appl. No.: 48,013

[22] Filed: Apr. 15, 1993

[51] Int. Cl.$^5$ .............................................. A61M 5/00
[52] U.S. Cl. .................................... 604/110; 604/218
[58] Field of Search .............. 604/110, 187, 218, 220, 604/228

[56] References Cited

U.S. PATENT DOCUMENTS

| | | | |
|---|---|---|---|
| 3,951,146 | 4/1976 | Arias | 604/110 |
| 5,034,002 | 7/1991 | Duranzampa et al. | 604/218 X |
| 5,257,976 | 11/1993 | Fenet | 604/110 |

*Primary Examiner*—John D. Yasko
*Attorney, Agent, or Firm*—Mason, Kolemainen, Rathburn & Wyss

[57] ABSTRACT

Throw-away syringe, of the type constituted by a cylindrical tubular body in which a stopper can be displaced in the direction of its axis being the latter controlled by a manually actuated stem and in the above syringe, between the stopper associated to the stem and the discharge end of the tubular body, is fitted freely a second stopper carrying a blade placed in an adequate setting of said stopper, a blade inoperative during the backward movement of the stopper and operative to make a mark or incision in the advance direction, a mark through which the inner pressure of the cylindrical body is equalled to the atmospheric pressure to prevent sucking out and therefore re-using the syringe after its first use.

6 Claims, 3 Drawing Sheets

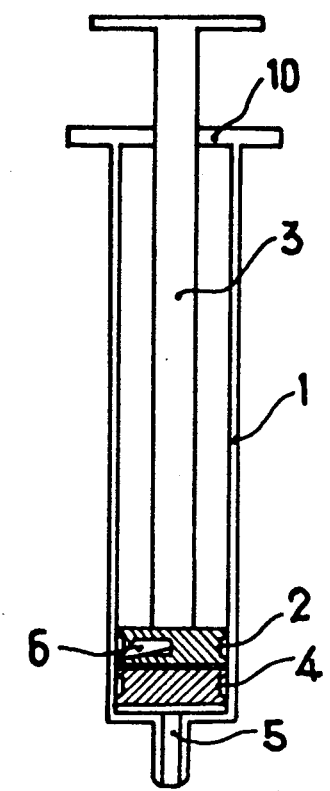
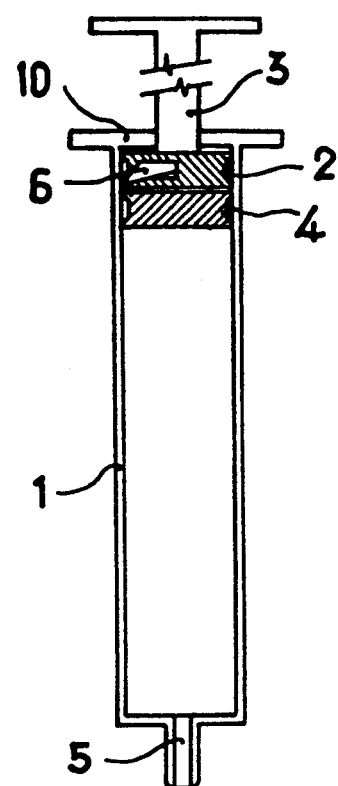
FIG.5  FIG.6
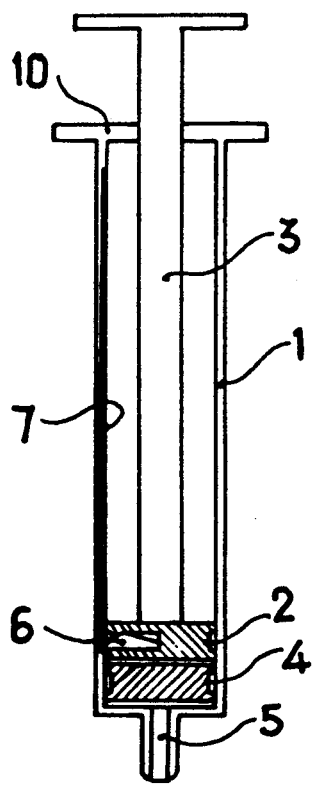
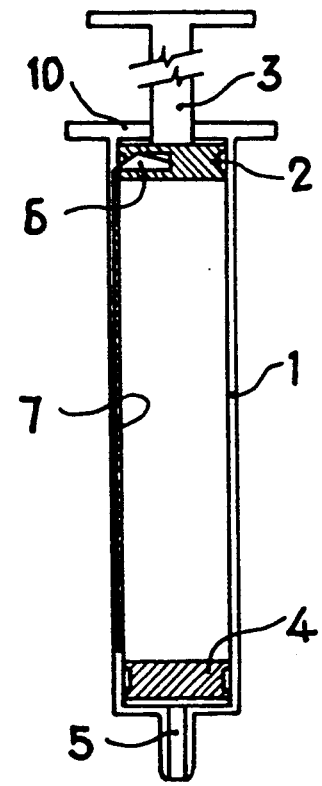
FIG.7  FIG.8

THROW-AWAY SYRINGE

The invention refers to a throw-away syringe, whose evident purpose is to be unserviceable after its first use with the aim to avoid infection risks derived from the use of syringes.

At present, and due to certain infectious diseases, medicine professionals or even private individuals tend to use throw-away syringes both for injections and for the extraction of blood and akin substances.

Even though for marketing purposes syringes are compulsorily designed for a single use, that is, they are considered throw-away items, many times they are re-used and this implies serious infection hazards.

At present, the manufactures are trying to provide the public and the market in general terms with syringes that cannot be re-used. Nevertheless, the results obtained are still very much wanting, often because it is not possible to obtain unusable syringes after being used for the first time, and other times because the means applied to render them unusable are complex and even practically inapplicable.

For this reason, we still do not know about a syringe that guarantees its spoilage after its first use.

There are different state-of-the-art patents regarding to throw-away syringes, with the purpose to avoid infection or accidents among its users.

Thus, the U.S. Pat. No. 4,391,273 claims a disposable non-reusable syringe, the U.S. Pat. No. 3,951,146 also claims an indestructible disposable syringe that makes impossible for it to be reused. The patent PCT NO. WO 90/07949 claims a disposable throw-away syringe and its manufacture procedure.

Though its designers describe the application of this syringes, in fact none of them is endowed with all the features and advantages derived from the concept and the structure of the syringe described in this application for an Invention Patent.

The aim of the invention is to obtain a syringe which, based in a simple solution, can be rendered unusable by itself, after its first and single use thus being impossible to reuse it.

More precisely, the syringe proposed has the peculiarity that, being based in a tube in which a stopper associated to an axial stem can be actuated on, both externally and manually, it incorporates a second stopper fitted freely inside the tube, between the bottom or the discharge end and the first stopper associated to the actuated stem.

Thus, when suction is effected, previously fitting both stoppers at the discharge end, both stoppers move along the syringe as a consequence of the vacuum generated. Nevertheless, when the contents of the syringe are injected, a blade adequately fitted to any of the two stoppers will make an cut or will leave a mark along the longitudinal axis in the tube, in such a way that, should the syringe be reused, it will not suck out because the free stopper will not travel, it will stay at the bottom or at the discharge end. This happens because the vacuum will not be made when absorbing air through the cut or mark made according to the above stated.

The cutting blade can be an independent element fitted to either of the two stoppers in an appropriate way to make the cut or the incision only during the movement of application of the injection, that is, towards the discharge end. Or also, this blade could also have a cutting portion which would be a part of the stopper itself.

To make it easier to understand the features of the invention, we are going to make a detailed description based on a set of drawings enclosed to this descriptive report which constitutes a pare to the same and in which, we have depicted with a merely suggestive and non restrictive character, the following:

Picture 1 shows the syringe of the invention with the blade fitted into the free stopper. Both stoppers are placed in the initial position.

Picture 2 shows the same syringe in suctioning position.

Picture 3 shows the syringe in the position of use. In it can be appreciated the mark or the cut made by the blade in its forward travel.

Picture 4 shows the same syringe with the stopper of the stem in the suction position, after being used, but the free stopper is immobile to prevent suction or re-utilisation of the syringe.

Pictures 5 to 8 show the syringe in the same use stages that the ones depicted in the four figures described above but with the blade fitted in the stopper associated to the actuation stopper.

Figure 1:
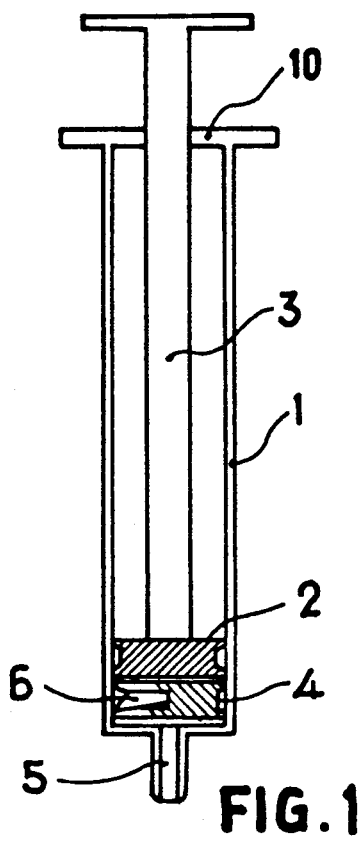
Figure 2:
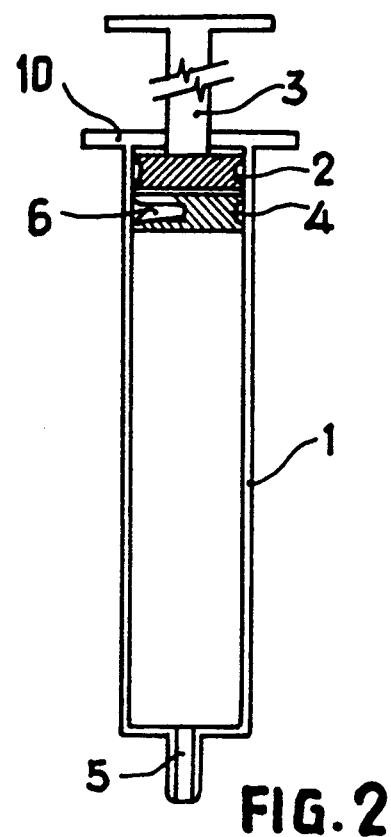
Figure 3:
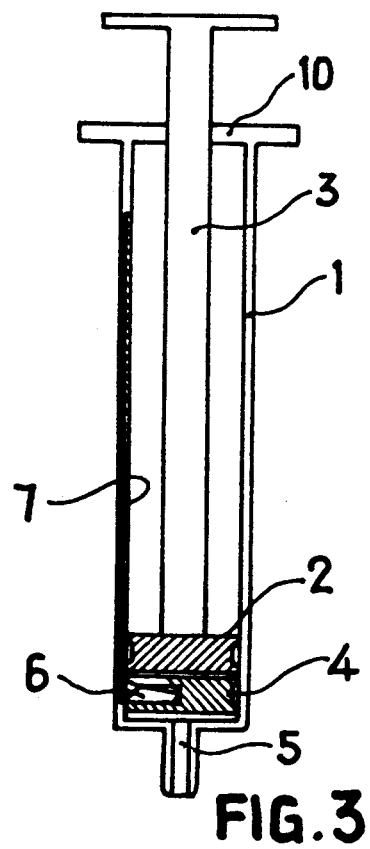
Figure 4:
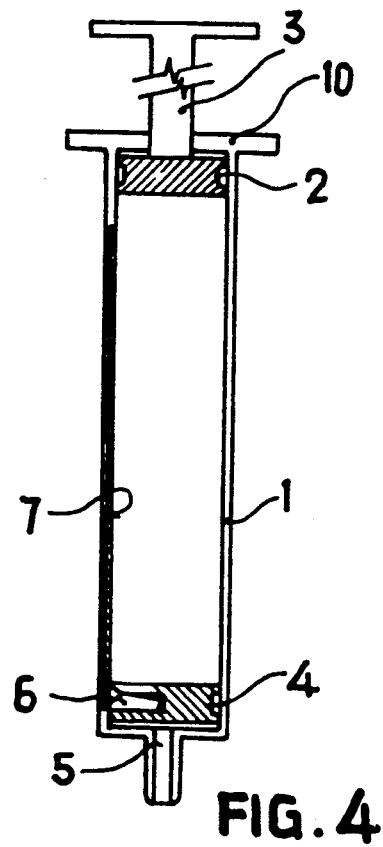

1. - Cylindrical tubular body of the syringe.
2.- Stopper
3.- Stem associated to the stopper (2).
4.- Free stopper.
5.- Discharge end of body (1).
6.- Blade.
7.- Incision or mark made by the blade (6).
8.- Incision appendix.
9.- Stopper of which the appendix is a part (8).
10.- Ring-shaped ledge of the mouth of the cylindrical body.

According to what the pictures show, the syringe of the invention consists of a cylindrical hollow body (1) and a stopper (2) associated to a actuator stem (3), the shopper (2) having stops inside the cylindrical body.

In addition, the syringe includes a second stopper (4) freely fit inside the body (1), between the stopper (2) and the discharge end (5) of the body (1) of the syringe.

The novelty is that either the second stopper (4), as shown in pictures 1 to 4 or the stopper (2) shown in pictures 5 to 8, have a seat where there is an adequately positioned blade (6), swivel-mounted in the seat so that in one of the directions of movement it will be rendered inoperative by itself whereas in the opposite, it will drive itself into the inner surface of the body (1) and will make in it a cut or a mark (7) corresponding to one of its generating lines as shown in pictures 3 and 4, or in pictures 7 and 8 and clearly in pictures 11 and 12. The direction in which it is inoperative is that of withdrawal of the stopper, whereas it is operative when advancing.

According to the above stated, the procedure of using and rendering unusable the syringe is as follows:

For sales purposes, stoppers 2 and 4 are placed at the end of the body (1), as shown by pictures 1 and 5. From that position, when the stem is pulled out (3) backwards, the appropriate liquid can be sucked out (either blood, liquid medicines, etc.) and the stopper (4) moves also backwards due to the vacuum generated, reaching the position of pictures 2 and 6. In this backward travel, the blade, (6) due to its position, configuration and swivelling doesn't make any cut. Afterwards, and when the stoppers are impulsed or pushed towards the opposite position, as shown in pictures 3 and 7, the blade (6), when moving makes an incision or a mark (7) into the body (1). If you try to re-use the syringe afterwards, there will not be any suction, because even though the stopper (2) is pulled backwards, the stopper (4) will not move, staying in the discharge end (5) as pictures 4 and 8 show. This immobilisation of the stopper is due to the fact that the inner pressure is equalled with the atmospheric, by means of the cut or mark (7) thus preventing generation of the vacuum necessary for suction. In addition, the above stopper (2), when pulling from the stem (3) towards the extraction position, will not be able to get out of the tubular body (1), because the mouth of the latter has a bottleneck determined by the inner ring ledge (10) foreseen for this purpose in the mouth, the stopper (2) is stopped by the ledge (10), thus preventing it from coming out, a feature that also renders the syringe unusable.

Figure 9:
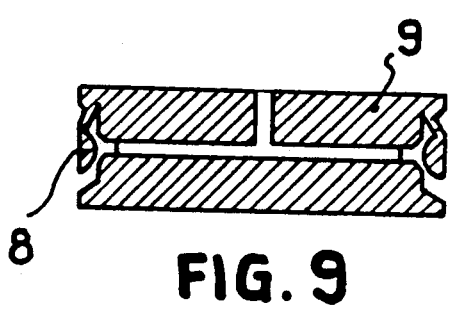
FIGS. 9 and 10 show the elevation views of a stopper in which the blade constitutes a part of it.
Figure 10:
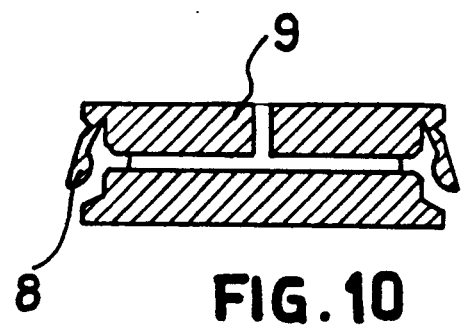
Figure 11:
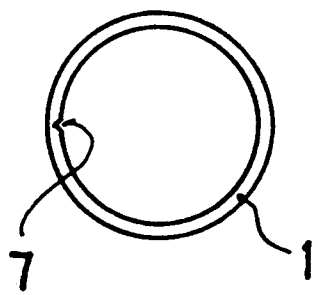
FIGS. 11 and 12 show the cross section and the cross perspective the cylindrical tubular body of the syringe, where it can be seen the cut or the mark left by the blade.
Figure 12:
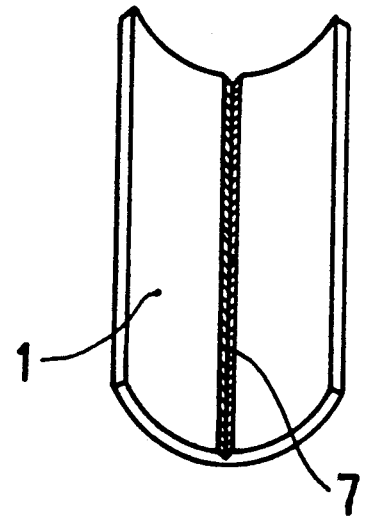

Finally, we would like to state that the blade, instead of being an independent element can be constituted by an elastic appendix (8) that belongs to the body of the stopper itself. This appendix is made of hard plastic material, and works in the same way as the blade (6); that is, it is inoperative backwards and operative in the direction of advance. FIGS. 9 and 10 show this possibility, both in the standstill or inoperative position and in the actuation or operative position of the appendix to make the mark or cut in the inner lateral surface of the tubular body of the syringe.

The fact that the syringe is not cut but only ripped in the inner part of its cylindrical tubular body, makes impossible an accident of infection by cut, and also the external contamination via the substance left inside the syringe. As a consequence of the features of this syringe, there are no residues or contaminant debris in the syringe.

I claim

1. A throw-away syringe, of the type including a cylindrical tubular body in which a first stopper is mounted to be displaced in the direction of an axis of said body as controlled by a manually actuated stem; said syringe including a second stopper between said first stopper and a discharge end of said tubular body freely movable in said body; a blade fitted above said second stopper, said blade inoperative during a backward stroke of movement of said second stopper and operative to make a mark or incision in said body when said second stopper is moved in an opposite advance direction, said mark in said body permitting the inner pressure in said cylindrical body to become equal to atmospheric pressure to prevent sucking up of fluid and therefore prevent reusing the syringe after its first use.

2. A throw-away syringe according to claim 1, characterized by the fact that the blade is fitted in a swivelling fashion to make it possible to render it inefficient or inoperative in one of the directions of movement and operative in the opposite direction of movement.

3. A throw-away syringe according to claim 1, characterized by the fact that the blade is fitted on the stopper associated to the stem.

4. A throw-away syringe according to claim 1 characterized because the blade is constituted by an elastic appendix which is a part of the body itself or is an essential part of the stopper.

5. A throw-away syringe according to claim 1, characterized because the mouth of the cylindrical tubular body has an inner ring-shaped ledge, which creates a stop to prevent the extraction of the stopper joined to the relevant actuated stem.

6. A throw-away, single use, syringe including a tubular body having a plurality of stoppers mounted therein for movement along an axis of said body, stem means connected to one of said stoppers for moving the same on a suction stroke toward a first end of said body to draw fluid into said body from a second end and on an injection stroke in an opposite direction for expelling said fluid from said body out said second end, the other of said stoppers being positioned in said body for free sliding movement along said axis between said ends; and knife means carried by at least one of said plurality of stoppers biased out of cutting engagement against an internal wall of said body when said stem means is moved on said suction stroke and engageable to cut a groove in said internal wall when said stem means is moved on said injection stroke for equalizing the pressure in said body with the surrounding atmosphere whereby said fluid will no longer be drawing into said body in response to a suction stroke of said stem means.

* * * * *